United States Patent [19]

Forster et al.

[11] Patent Number: 4,833,322

[45] Date of Patent: May 23, 1989

[54] METHOD AND APPARATUS FOR ANALYSIS OF MATERIAL

[75] Inventors: Alan R. Forster, Houston; Robert A. Howard, Missouri City; Ernest P. Williams, Houston, all of Tex.

[73] Assignee: Shell Oil Company, Houston, Tex.

[21] Appl. No.: 859,094

[22] Filed: May 2, 1986

[51] Int. Cl.[4] .............................................. G01N 21/73
[52] U.S. Cl. ..................................... 250/288; 356/36; 356/316
[58] Field of Search ................. 356/36, 306, 311, 315, 356/316, 417; 250/288, 281

[56]  References Cited
U.S. PATENT DOCUMENTS

| | | | |
|---|---|---|---|
| 3,032,654 | 5/1962 | Fay et al. | 356/306 |
| 3,586,446 | 6/1971 | Findl et al. | 356/36 |
| 3,759,617 | 9/1973 | Barringer | 356/316 |
| 3,843,257 | 10/1974 | Wooten | 356/316 |
| 4,136,951 | 1/1979 | Macourt | 356/36 |
| 4,221,482 | 9/1980 | Macourt | 356/316 |
| 4,330,295 | 5/1982 | Taylor et al. | 23/230 |
| 4,532,219 | 7/1985 | Hagen et al. | 356/316 |
| 4,556,318 | 12/1985 | Barnes et al. | 356/316 |
| 4,629,940 | 12/1986 | Gagne et al. | 219/121 D |

OTHER PUBLICATIONS

Mitchell et al., *Analytical Chemistry*, vol. 49, No. 8, Jul. 1977, pp. 1235-1238.
H. Matusiewicz and R. M. Barnes, An Electrothermal Sample Introduction System for ICP Spectrometry, Applied Spectroscopy, Vol. 38, No. 5, 1984, pp. 745-747.
K. C. Ng and J. A. Caruso, Electrothermal Vaporization for Sample Introduction in Atomic Emmision Spectrometry, Applied Spectroscopy, Vol. 39, No. 4, 1985, pp. 719-726.
W. M. Blakemore, P. H. Casey, and W. R. Collie, Simultaneous Determination of 10 Elements in Wastewater, Plasma Emission Spectrometry with Electrothermal Atomization, Analytical Chemistry, 56, 1984, pp. 1376-1379.

*Primary Examiner*—F. L. Evans

[57] ABSTRACT

Methods and apparatus are provided for qualitative and quantitative determination of constituents of a sample of material. The method prepares the sample for analysis by mixing the sample with a preselected quantity of a preselected material that serves to transport and project the sample. The mixture may be pyrolyzed and/or injected into a plasma. A spectrometric detection is made of the sample in the plasma. The apparatus is a modified electrothermal vaporization furnace whose sample outlet is connected to the sample inlet of an inductively-coupled plasma-mass spectrometer (ICP-MS). An additional gas (oxygen) injection line is provided between the sample outlet of the furnace and the sample inlet of the ICP-MS.

16 Claims, 5 Drawing Sheets

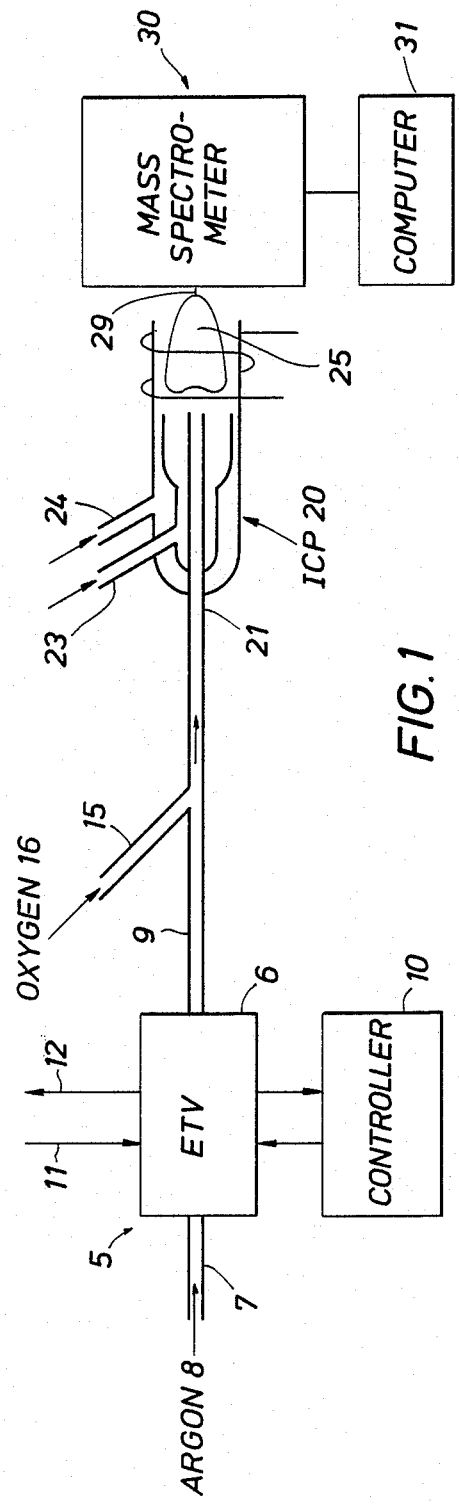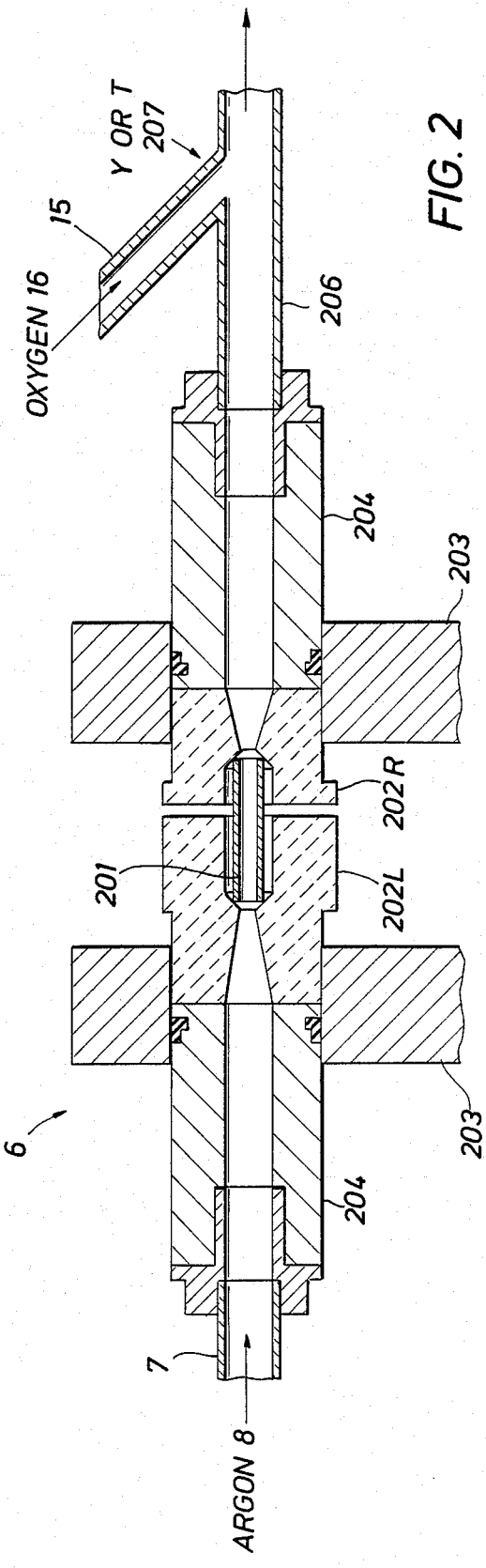

METHOD AND APPARATUS FOR ANALYSIS OF MATERIAL

BACKGROUND OF THE INVENTION

This invention relates to analysis of materials, and more particularly, relates to method and apparatus for the qualitative and quantitative determination of constituents of materials.

The spectral analysis of small particles of a specific material may be accomplished by introducing these particles directly into a plasma. The high temperature and high energy conditions found in a plasma may then cause the molecules and atoms to emit their characteristic spectra which can usually be readily identified.

Plasmas of excited gases may be generated by a variety of means including chemical flames, arc or spark discharges, inductively coupled radio frequency, and microwave-sustained gas discharges and may use support and/or excitation gases such as argon, helium, nitrogen, or oxygen.

Most plasma analysis techniques employ a carrier gas to carry a volatile particulate or gaseous sample to the plasma. However, use of a carrier gas to transport particles to and from the plasma usually results in certain shortcomings. More specifically, particulate fragments may recombine or condense on the conduit walls or may be adsorbed on the walls of the pyrolysis chamber and any transporting conduit. This usually results in a loss of material and "ghosting" or "memory effect" of materials, i.e. materials are adsorbed on the various sample transfer conduits and other interior surfaces and are introduced into the plasma during subsequent sample analysis which may result in spurious, erroneous analytical results. This loss of part of the sample, combined with an additional difficulty of maintaining reproducible pyrolysis temperatures and other conditions, makes it extremely difficult to obtain reproducible quantitative results.

Other problems may be associated with specific types of samples. As noted in U.S. Pat. No. 4,532,219, it is usually impossible to completely volatilize organic samples during pyrolysis without losing some portion of the sample to the walls of the pyrolysis apparatus and to any transfer conduits. The volatilization of a sample without the usual charring step is taught by "Simultaneous Determination Of 10 Elements In Waste Water, Plasma, and Bovine Liver By Inductively Coupled Plasma Emission Spectrometry With Electrothermal Atomization", Blakemore et al, Anal. Chem., 56, (1984) pp 1376–1379, but does not deal with organic samples.

Another technique that is common in the prior art is to aspirate and atomize or nebulize non-volatile material into a plasma. When materials are introduced into the plasma by aspiration, nebulization, atomization, or even directly more subtle problems may arise. For example, when an aerosol reaches a plasma, the aerosol may absorb energy from the plasma and as a result, may seriously affect plasma operating conditions and performance. In an extreme case, sample introduction may overload the plasma sufficiently to extinguish it entirely. A survey of electrothermal vaporization techniques for samples employed in atomic emission spectroscopy is found in "Electrothermal Vaporization for Sample Introduction in Atomic Emission Spectrometry", NG et al, Applied Spectroscopy Vol. 39, No. 4 (1985), pp 719–726.

These and other limitations and disadvantages of the prior art are overcome by the present invention, however, and improved methods and apparatus are provided for analysis of samples.

SUMMARY OF THE INVENTION

In a preferred embodiment of the present invention, methods and apparatus are provided for the qualitative and quantitative determination of constituents of samples. In the presently preferred method for the analysis of a sample, the sample is first prepared for analysis by mixing the sample with a preselected quantity of a preselected material; the preselected material may serve to transport and protect the sample. This mixture of the sample and the material may then be pyrolyzed (i.e. broken down into simpler components by heat or other radiation) and after such pyrolyzation may be appropriately transported to a plasma by a carrier gas. The mixture is injected into the plasma and a spectrometric detection is made of the analyte, or preselected constituents of the sample injected into the plasma.

The sample to be analyzed by the method of the present invention may be a liquid or solid and may be an inorganic or organic specimen, as well as being volatile or non-volatile. The method of the present invention is preferably used with small sample quantities. In particular for solid samples, the particles of the solid must be comminuted into particles of about a micron in size.

The presently preferred apparatus of the present invention is a modified ElectroThermal Vaporization (ETV) device whose sample output is coupled to the sample input of an Inductively-Coupled Plasma (ICP) whose output in turn is coupled to a mass spectrometer. Further, the apparatus of the present invention has an additional carrier gas injection line between the ETV and ICP which injects oxygen, to combust the preselected material, into the gas stream from the ETV sample outlet.

It is the object of the present invention to provide an apparatus for quantitative and qualitative analysis of a sample.

It is also an object of the present invention to provide a method for quantitative and qualitative analysis of a sample.

It is a specific object of the present invention to provide a method of analysis for preselected constituents of a sample, comprising, providing a sample excitation means, preparing said sample for analysis by mixing said sample with a preselected quantity of a preselected material, injecting said mixture of said sample and said material into said sample excitation means, and then performing spectrometric detection of said mixture in said sample excitation means.

It is also a specific object of the present invention to provide a method for determining the amount of preselected constituents in a biological sample, comprising, providing a sample excitation means, pyrolyzing said sample, transporting said pyrolyzed sample to said sample excitation means, injecting said pyrolyzed sample into said sample excitation means, and then performing spectrometric detection of said pyrolyzed sample in said sample excitation means.

It is yet a further specific object of the present invention to provide an apparatus for determining the qualitative presence and quantitative amounts of preselected constituents in a sample, comprising, sample excitation means, means for monitoring said sample excitation means for the qualitative and quantitative presence of preselected constituents, first source of carrier gas, sample chamber means interconnected with said first source of carrier gas and with said sample excitation means to provide a flow of carrier gas from said first source of carrier gas through said sample chamber and into said sample excitation means, heating means located in said sample chamber means for pyrolyzing a sample located in said sample chamber, second source of carrier gas, and means for injecting said second carrier gas into said flow of said first carrier gas between said sample chamber means and said sample excitation means.

These and other features, advantages and objects of the present invention will become apparent from the following detailed description, wherein reference is made to the figures in the accompanying drawings.

IN THE DRAWINGS

FIG. 1 is a simplified functional diagram of one embodiment of the apparatus of the present invention.

FIG. 2 is a simplified functional diagram of one portion of the apparatus depicted in FIG. 1.

DETAILED DESCRIPTION OF THE INVENTION

Figure 3:
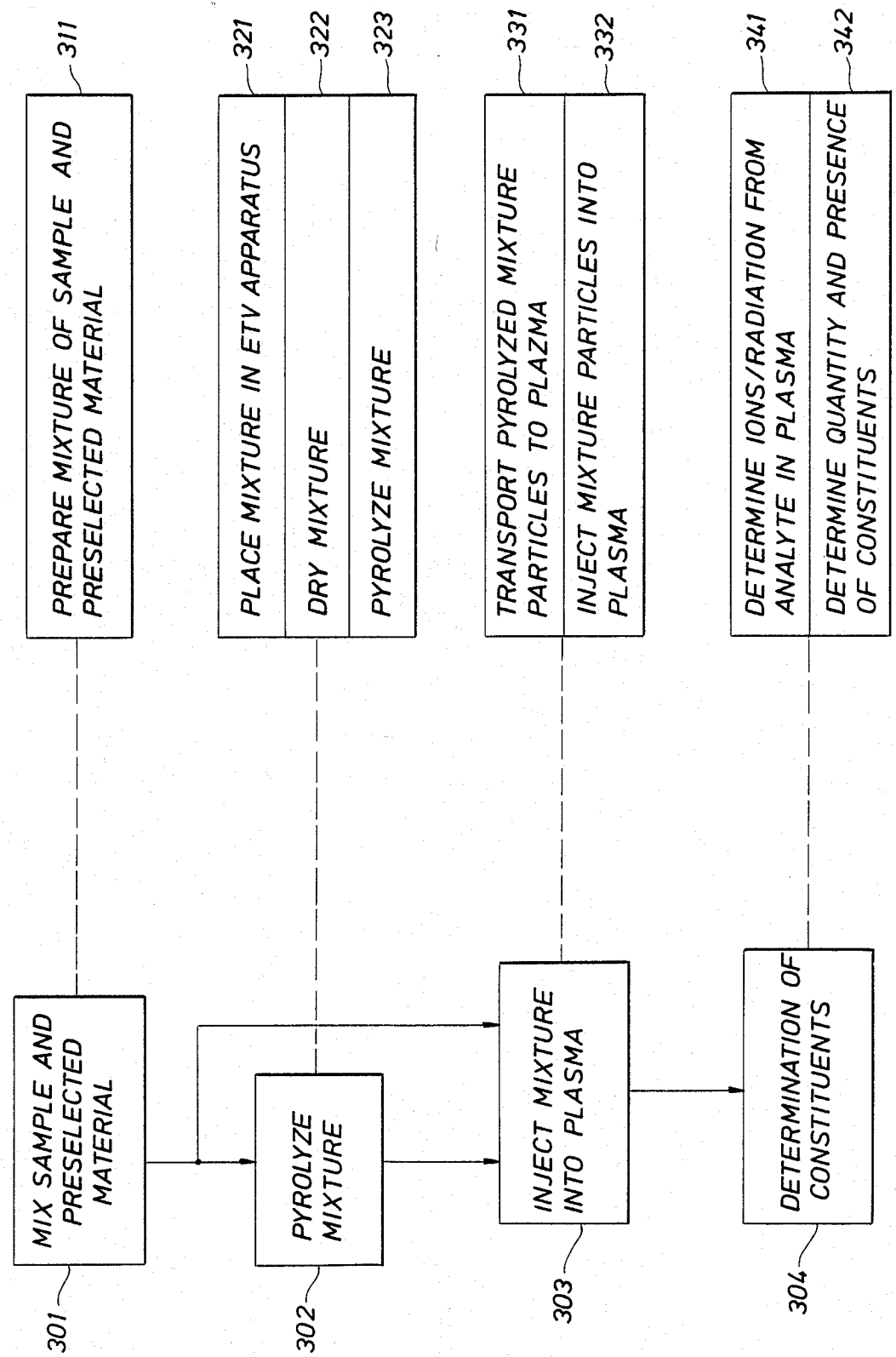
FIG. 3 is a simplified flow diagram of the preferred method of the present invention.

The present invention provides methods and apparatus for qualitative and quantitative determinations of preselected constituents of a sample. The description of the apparatus and methods of the present invention herein employs the following terms to have the following meanings: "pyrolyze" or "pyrolysis" and any derivatives thereof means the breaking down of a substance into simpler components by heat or other radiation; "analyte" means those preselected constituents of a sample sought to be detected; "sample excitation means" means a means for volatilizing, vaporizing, atomizing, pyrolyzing, exciting and/or ionizing a sample; "spectrometric detection" means detecting ions or radiation associated with preselected constituents of a sample and determining therefrom qualitatively and quantitatively such preselected constituents; and "mixture" means a sample and preselected material, whether or not preselected material must be separately added to the sample.

Referring now to FIG. 1, there may be seen a simplified functional diagram of one embodiment of the apparatus of the present invention. More specifically, it may be seen that the presently preferred apparatus of the present invention consists of ElectroThermal Vaporization (hereinafter ETV) furnace assembly 5 operatively interconnected to Inductively-Coupled Plasma (hereinafter ICP) assembly 20, which is in turn operatively interconnected to Mass Spectrometer 30, sometimes hereinafter referred to as MS.

Continuing to refer to FIG. 1, it may be seen that the ETV furnace assembly 5 consists of the actual ETV furnace 6, suitably modified as discussed later herein, an associated carrier or cooling gas inlet line 7, which preferably employs argon 8, and a gas outlet line 9. A sample is placed in the ETV furnace, as discussed later herein, and is pyrolyzed therein and exists in a carrier gas stream through outlet line 9. Also depicted in FIG. 1 are cooling water inlet and outlet lines, respectively 11 and 12. Controller 10 may control the temperatures and rates of temperature increase for the ETV furnace 6.

As shown in FIG. 1, the sample (after pyrolysis), and carrier gas stream from the ETV furnace assembly 5 is provided to an ICP assembly 20. The ICP assembly 20 has a sample and/or carrier gas inlet 21, which preferably employs argon. The ICP assembly also has an auxiliary gas flow inlet 23 and coolant gas flow inlet 24.

As depicted in FIG. 1, there is an additional carrier gas injection line 15 which allows for the injection of an additional carrier gas into the sample and carrier gas outlet line 9 of the ETV furnace assembly 5, via "Y" or "Tee" connection in line 9. Preferably, the gas flowing through this additional gas injection line is oxygen 16. Oxygen is employed to combust the preselected material, as described more fully later herein. The combined carrier gas from the injection line 15 and from ETV furnace assembly 5 in its outlet line 9 is provided as the carrier gas to the ICP assembly 20. The ICP assembly contains a plasma 25. The carrier gas and sample from the ETV furnace, and the additional carrier gas from the additional carrier gas injection line may be atomized, excited and/or ionized in the plasma 25 of the ICP assembly 20 and are preferably provided as an ionized gas stream 29 to the mass spectrometer 30. As noted hereinbefore, the term "analyte" is used herein to mean those preselected constituents of a sample sought to be detected.

ICP devices are commercially available and may be obtained from many companies including: ARL (Applied Research Labs) of Sunland, Calif.; Perkin-Elmer of Norwalk, Conn.; Leeman Labs of Lowell, Mass.; Instruments S.A. of Metuchen, N.J.; Allied Analytical of Waltham, Mass.; and R. F. Plasma Products of Cherry Hill, N.J.

As depicted in FIG. 1 the mass spectrometer 30 may have associated therewith a controller and/or computer 31 which controls the operation of the mass spectrometer.

Mass spectrometers are commercially available and may be obtained from many companies, including: Hewlett-Packard of Avondale, Pa.; Finnigan MAT of San Jose, Calif.; and Balzers of Hudson, N.H.; and combined ICP-MS apparatus are commercially available from: VG Isotopes Ltd. of Winsford (Cheshire) England and SCIEX Ltd. of Toronto, Canada.

The modified arrangement of the ETV furnace 6 of FIG. 1 is depicted in more detail in FIG. 2. Referring now to FIG. 2, a conventional graphite furnace tube 201 may be modified by plugging or eliminating the usual through-wall hole (not shown) located in the center of the tube. Additionally, the inner surface of the tube is preferably smooth throughout its entire interior length. The furnace tub 201 is placed between graphite cones 202L, 202R which in turn are press-fit into furnace electrodes 203; the positions of graphite cones 202L, 202R may be exchanged from that depicted, if desired. The furnace electrodes may be contained in a mechanism (not shown) that may be held closed by a compressed-gas-actuated piston (not shown). Appropriate valving (not shown) and a second piston (not shown) allow for opening of the mechanism so that the furnace tube may be replaced. Aluminum connection tubes 204 are pressed into the concentric openings (where quartz windows normally reside) at the opposite ends of electrodes 203 using O-ring seals. Inlet argon tube 7 is connected to the left side of the furnace connection tube 204 using a PTFE compression fitting. Outlet gas from the right side of the furnace travels through glass tube 206 which is connected to the right side aluminum connection tube 204 using a PTFE compression fitting. These connections may also be reversed, if desired. Other modifications may be made, as suggested in, "An Electrothermal Sample Introduction System For ICP Spectrometry", Barnes et al, Applied Spectroscopy, Vol. 38, No. 5, (1984) pp 745–747. A glass, tygon, metal, quartz, PTFE or plastic "Y" or "Tee" 207 may be connected at the outlet of glass tube 206. The outlet of the "Y" 207 is connected to additional transfer tubing which can be made of glass, plastic, quartz, PTFE, or metal, and is in turn connected to the ICP assembly. A protectant flow of argon is also directed around the outside of the furnace tube 201 to protect it from oxidation. An oxygen supply and flow 16 (See FIG. 1) is provided for the "Y" 207. These various tubes and fittings provide a continuous gas-tight flow chamber from the gas inlet line of the ETV furnace to the plasma.

In operation, a sample and its preselected material of preselected quantity are introduced into the interior of tube 201 and deposited on an interior wall of tube 201. If the sample and preselected material are liquid then the sample and material may be pipetted into the tube 201 by removing left connector tube 204 to provide access to the interior of tube 201. If the sample and material form a paste or are a solid they may be placed on a sample boat and placed in the interior of tube 201 by forceps or other appropriate means. Alternatively, the tube 201 may be removed from the assembly 6, the sample and material deposited therein, and then reinserted into assembly 6.

After the sample and material are placed in tube 201 and the other associated equipment are operating, the carrier gas to assembly 6 is turned on, if it was turned off during sample placement. The carrier gas flow rate is about two liters per minute. However, the carrier gas flow rate may be from about 0.5 L/min to about 5.0 L/min. The furnace assembly 6 may then be slowly heated to dry out the sample and material mixture. Then the furnace is rapidly ramped up in temperature to about 2500° C. in about one second and held there for about six seconds and is then ramped up to about 2700° C. in about one second and held there for about five seconds. These ramp rates are presently believed to be minimum rates and faster ramp rates may be acceptable. These times and temperatures may be appropriately preset in the controller 10 of furnace assembly 6.

ETV furnaces are commercially available from Allied Analytical [formerly Instrumentation Labortory] (model IL655) and Perkin Elmer (models HGA74 to HGA500). Although the preferred embodiment described hereinbefore employs an ETV furnace, other ETV devices, or a laser, or a second plasma may be so employed in the place of the hereinbefore described ETV furnace.

The preferred method of the present invention may be practiced in the preferred apparatus of the present invention as described hereinabove, or other apparatus appropriately modified. Referring now to FIG. 3, there may be seen a simplified flow chart of the methods of the present invention. The main steps 301–304 are depicted on the left of FIG. 3, while the steps are the right of FIG. 3 detail the increments of these main steps. The first step of the presently preferred method of the present invention is to prepare the sample for pyrolyzation by adding a preselected quantity of a preselected material to the sample for solid or liquid samples 301, 311; gaseous samples may be passed directly into a plasma, as is well known in the art. This preselected quantity is from about 0.1 mg (or 0.1 μL) to about 10 mg (or 10 μL) depending upon the sample size and sample type. The total mixture of sample and material should not exceed about 10 mg or 10 μL, or such larger quantity as may be safely consumed by the plasma source or other sample excitation means employed to practice the method of the present invention. As presently understood, this preselected material may be selected based on the following characteristics:

(1) preferably, the material may rapidly and efficiently pyrolyze before it boils;

(2) the material may be free of or have minimal contamination in the mass or spectra of interest;

(3) optionally, the material is preferably organic; and (4) optionally, the material may be water soluble.

As noted hereinbefore, the term "pyrolyze" or "pyrolysis" and any derivatives thereof are used herein to mean the breaking down of a sustance into simpler components by heat or other radiation.

Although described hereinabove as if the preselected material is a separate material to be added to a sample, it is also possible for a preselected material to be a natural part of the sample and thus eliminate the need to add any additional preselected material to the sample. For biologic materials, there may be enough preselected material occurring in the sample naturally to preclude the need to add additional preselected material. However, if a sample does not contain a preselected material or a sufficient quantity of preselected material, preselected material must be added to the sample. As noted hereinbefore, the term "mixture" is used herein to mean a sample and preselected material, whether or not the preselected material has to be separately added to the sample. An actual example of such a biologic sample is discussed later herein.

This mixture of the sample and the preselected material is appropriately placed in the sample holding portion, as described hereinbefore, of the ETV furnace 321. The ETV furnace is then operated to pyrolyze the mixture 302, which may be a liquid, solid or paste, to a gaseous mixture of particulate and aggregates, which is then carried away by the carrier gas of the furnace. The mixture may also be dried 322, as appropriate, before pyrolysis of the mixture. The preselected material serves to protect the analyte to be analyzed during the pyrolysis in the furnace, as well as forming free and open, large surface area, particulate matter or aggregates containing the analyte, that may be easily carried by the carrier gas. Further, the preselected material in its large particulate or aggregate form serves to keep the analyte and other materials off the walls of the various conduit and chambers associated with the furnace and subsequent apparatus.

The carrier gas through the ETV furnace unit 5 is used to carry the pyrolyzed mixture to a plasma or other sample excitation means 331. The carrier gas also serves to cool and condense the pyrolyzed particulate mixture to prevent any further pyrolysis of the analyte, in addition to transporting this particulate mixture into the plasma 332.

The additional carrier gas, preferably oxygen, is employed to combust the organics of the pyrolyzed particulate mixture to avoid elemental carbon from condensing and depositing on the ion optics of the preferred means for monitoring the sample excitation means, a mass spectrometer, as noted hereinbefore.

Once in the plasma or other sample excitation means the particulate mixture may be volatilized, vaporized, atomized, excited and/or ionized in the plasma. The preselected material also serves to perturb the plasma in a reproducible manner independent of the type or quantity of analyte contained therein. A spectrometric determination is then made of the pyrolyzed mixture in the plasma, or other sample excitation means 304.

Preferably, an ion beam consisting of the analyte and other material is passed into mass spectrometer 30 in which ions may be detected 341. These ions are characteristic of the preselected constituents of the analyte. Thus, based upon the ions detected, the constituents qualitatively present may be determined and by appropriate integration and calibration a quantitative determination of the amount of those constituents in the sample 342 may be made.

As noted hereinabove, the term spectrometric detection, as used herein includes the steps of detecting the associated ions or radiation from the mixture in the plasma and determining therefrom the qualitative and quantitative constituents of the sample. In particular, spectrometric detection is meant to include, by way of example, but is not limited to, atomic absorption, atomic emission, atomic fluorescence, laser enhanced ionization, and mass spectrometry.

Although the preferred method of the present invention has been described above, other alternative methods fall within the scope of the invention. One such alternative method of the present invention is depicted in FIG. 3 and employs the same initial step of mixing the sample with a preselected quantity of a preselected material. However, this mixture of the sample and preselected material is then injected directly into a plasma which serves to pyrolyze, volatilize, vaporize, atomize, excite and ionize the sample in the plasma. A spectrometric detection may then be performed on the mixture in the plasma, as described hereinabove, to qualitatively and quantitatively determine preselected constituents of the sample.

Further, the method also applies to any effective sample excitation means or plasma source which may be, but not limited to, a flame, an arc, or microwave energy.

Thus, the present invention provides both a qualitative and quantitative determination of preselected constituents of a sample. In accordance with the teachings of the preferred method of the present invention, a sample and its preselected material are pyrolyzed, then injected into a plasma, and a spectrometric determination of the analyte is then made. This analysis of analyte is both reproducible and quantitative.

The following example is illustrative of the methods and apparatus of the present invention, but is exemplary only and is not to be construed or interpreted as limitations on the scope of the invention.

EXAMPLE 1

The equipment employed consisted of a Perkin-Elmer HGA-500 grahite furnace (modified as described hereinabove), and a SCIEX Elan 250 (elemental analyzer-ICP/MS). The furnace outlet was a glass tubing connected to a plastic "Y" with tygon tubing around the connection. The outlet of the "Y" was connected to the inlet of the ICP-MS with tygon tubing. The other inlet of the "Y" was connected to a compressed cylinder of oxygen, via an appropriate cylinder regulator and flow controller, with tygon tubing.

The sample to be analyzed consisted of human, recovered, chronic, lymphocytic, leukemia cells. Approximately ten thousand cells of this sample were mixed with about 0.17 g of hyamine hydroxide. The hyamine hydroxide was added as the preselected material and also serves to create a homogeneous and uniform mixture. This hyamine hydroxide and cell mixture was then diluted with deionized water to about 1.0 mL. 10 $\mu$L of this mixture were transferred to the interior of the furnace tube, as described hereinbefore.

The furnace was operated at about 2 L/min of argon gas flow through the furnace tube. The furnace was ramped up to about 90° C. over about ten seconds and held at this temperature for about one minute. Then the auxiliary carrier gas was turned on to a flow rate of about 0.3 L/min; for this sample oxygen was employed as the auxiliary carrier, as noted hereinbefore.

The ICP/MS was programmed to acquire data for 150 cycles (each cycle consists of 25 millisec integration periods for each of three preselected mass determinations for this sample). The ICP/MS was operated at about 1.25 kW and was sampled about 2 cm above the load coil. The argon gas coolant flow rate for the ICP/MS was about 12 L/min and the auxiliary argon gas flow rate for the ICP/MS was about 2 L/min.

The furnace began its ramp up and the ICP/MS data collection was begun at the same time; the furnace was ramped up to about 2500° C. in about one second and held at that temperature for about six seconds. The furnace was then ramped up to about 2700° C. in about one second and held at that temperature for about five seconds, after which the furnace is turned off. Data were allowed to be collected by the ICP/MS for the 150 cycles. The auxiliary carrier gas (oxygen) was then stopped.

Figure 4:
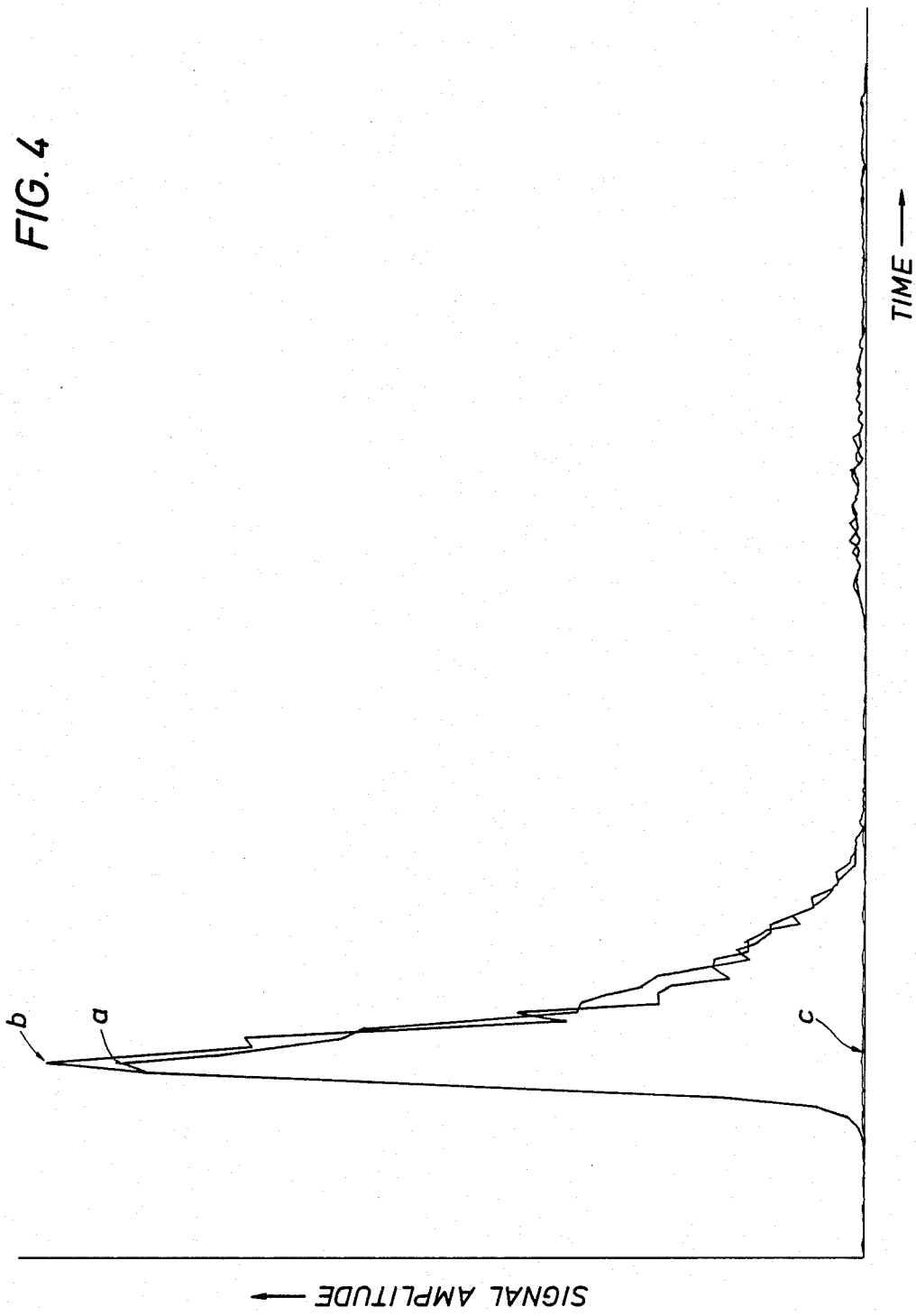
FIG. 4 is a simplified representation of data collected by the preferred embodiment of the present invention illustrating the presence of a preselected constituent of a sample.
Figure 5:
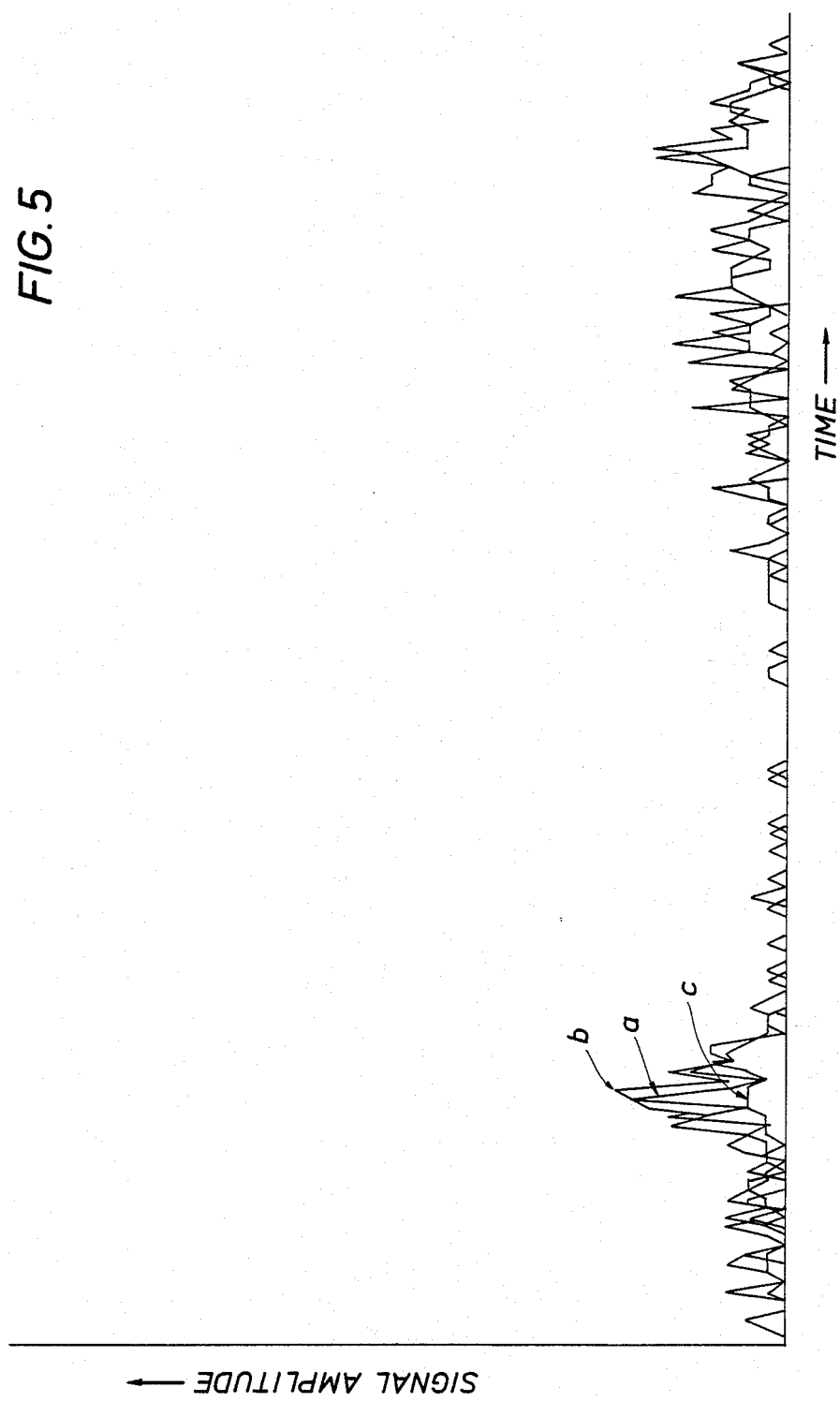
FIG. 5 is a simplified representation of data collected by the preferred embodiment of the present invention illustrating a background for the constituents of FIG. 4.
Figure 6:
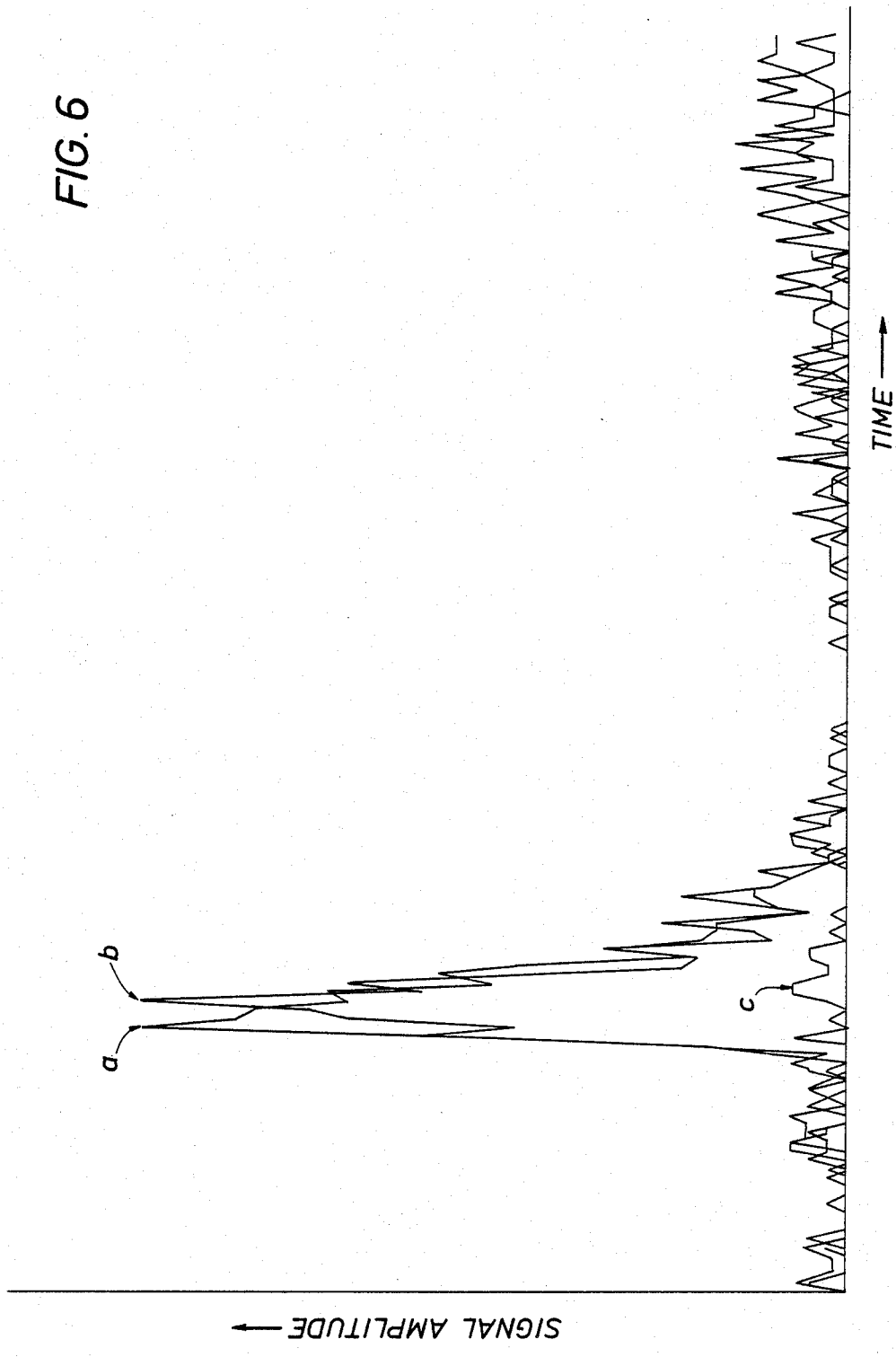
FIG. 6 is a simplified representation of data collected by the preferred embodiment of the present invention illustrating a control sample spiked with the preselected constituent of FIG. 4.

FIG. 4 depicts data collected as described hereinabove which indicates the presence of platinum isotopes 194 (curve a) and 195 (curve b) in the sample; mass 193 (curve c) was employed as a background check to ensure no spurious signals were caused by organic materials or plasma emissions. FIG. 5 depicts data collected as described hereinabove with control cells (cells from patients having no cis-platin [cis-diamminedichloroplatinum] treatments) which followed several analyses of cells from patients treated with cis-platin to verify no "memory effect" or sample "ghosting", as well as no platinum signal in the control cells. FIG. 6 depicts data collected as described hereinabove employing control cells "spiked" with three pico-grams of platinum.

Based upon these and other analysis runs of the sample, the detection limit, whose meaning is well known in the art, was calculated to be 0.05 pico-grams of platinum.

Many other variations and modifications may be made in the apparatus and techniques hereinbefore described, by those having experience in this technology, without departing from the concepts of the present invention. Accordingly, it should be clearly understood that the apparatus and methods depicted in the accompanying drawings and referred to in the foregoing description, are illustrative only and are not intended as limitations on the scope of the invention.

What is claimed is:

1. A method of analysis for preselected constituents of a sample comprising:
   providing a sample excitation means,
   preparing a portion of said sample for analysis by mixing said portion of said sample with a preselected quantity of a preselected material,
   injecting said mixture of said sample and said material into said sample excitation area means to reproducibly perturb said sample excitation means, and then
   performing spectrometric detection of said mixture in said sample excitation means for at least one of said constituents of said sample.

2. A method as described in claim 1 further comprising: pyrolyzing the mixture of said sample and material before injecting said pyrolyzed mixture into said sample excitation means.

3. A method as described in claim 2 further comprising: transporting said pyrolyzed mixture to said sample excitation means.

4. A method as described in claim 1 wherein said spectrometric detection step comprises:
   detecting radiation or ions associated with said mixture in said sample excitation means, and
   determining said preselected constituents and quantities of said constituents of said sample from said detected radiation or ions.

5. A method as described in claim 2, further comprising drying said mixture before said pyrolysis step.

6. A method as described in claim 1, wherein said sample comprises an organic sample.

7. A method as described in claim 1, wherein said sample comprises a biologic sample.

8. A method described in claim 1, wherein said sample excitation means comprises a plasma.

9. A method for determining the amount of preselected constituents in a biological sample containing a preselected material, comprising:
   providing a sample excitation means,
   pyrolyzing a portion of said sample and preselected material,
   transporting said pyrolyzed sample and preselected material to said sample excitation means,
   injecting said pyrolyzed sample and preselected material into said sample excitation means to reproducibly perturb the sample excitation means, and then
   performing spectrometric detection of said pyrolyzed sample in said sample excitation means for at least one of said constituents of said sample.

10. Apparatus for determining the qualitative presence and quantitative amounts of preselected constituents in a sample, comprising:
    sample excitation means,
    means for monitoring said sample excitation means for the qualitative and quantitative presence of preselected constituents,
    first source of first carrier gas,
    sample chamber means interconnected with said first source of first carrier gas and with said sample excitation means to provide a flow of first carrier gas from said first source of carrier gas through said sample chamber into said sample excitation means,
    heating means located adjacent said sample chamber means for pyrolyzing a sample located in said sample chamber means,
    second source of second carrier gas, and
    means for injecting second carrier gas from said second source of carrier gas into said flow of said first carrier gas between said sample chamber means and said sample excitation means.

11. The apparatus as described in claim 10, wherein said sample excitation means comprises a plasma.

12. The apparatus as decribed in claim 11, wherein said means for monitoring said sample excitation means comprises a mass spectrometer.

13. The apparatus as described in claim 12, wherein said second source of carrier gas comprises a source of oxygen.

14. The apparatus as described in claim 13, wherein said sample chamber means and heating means located therein comprise an electrothermal vaporization furnace.

15. The apparatus as described in claim 14, wherein said first source of carrier gas comprises a source of argon.

16. A method for determining the amount of preselected constituents in a biological sample, comprising:
    providing a sample excitation means,
    adding a preselected material to a portion of said biological sample to form a mixture,
    pyrolyzing said mixture,
    transporting said pyrolyzed mixture to said sample excitation means,
    injecting said pyrolyzed mixture into said sample excitation means to reproducibly perturb the sample excitation means, and then
    performing spectrometric detection of said pyrolyzed mixture in said sample excitation means for at least one of said constituents of said sample.

* * * * *